United States Patent [19]

Cairns et al.

[11] 4,211,788
[45] Jul. 8, 1980

[54] COMPOUNDS

[75] Inventors: Hugh Cairns, Loughborough; Anthony R. Payne, Castle Donington, both of England

[73] Assignee: Fisons Limited, London, England

[21] Appl. No.: 904,794

[22] Filed: May 11, 1978

[30] Foreign Application Priority Data

May 21, 1977 [GB] United Kingdom ............... 21545/77

[51] Int. Cl.² .................. A61K 31/355; C07D 311/22
[52] U.S. Cl. .................................. 424/283; 260/345.2; 542/429; 548/251; 548/253
[58] Field of Search ...................... 260/345.2; 424/283

[56] References Cited

U.S. PATENT DOCUMENTS

| 3,427,324 | 2/1969 | Fitzmaurice | 260/345.2 |
| 3,484,445 | 12/1969 | Lee et al. | 260/345.2 |

Primary Examiner—Nicky Chan
Attorney, Agent, or Firm—Merriam, Marshall & Bicknell

[57] ABSTRACT

There are described compounds of formula I,

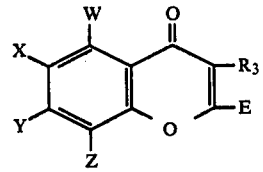

in which E is a —COOH, a 5-tetrazolyl or an (N-tetrazol-5-yl) carboxamido group,
  $R_3$ is hydrogen or alkyl,
  an adjacent pair of W, X, Y and Z form a 5 membered chain comprising alkylene groups and optionally one or two oxygen atoms, the chain optionally being substituted by one or two alkyl groups,
  the remaining substituents W, X, Y or Z are hydrogen; halogen; alkyl optionally substituted by one or more of the groups hydroxy, halogen, carbonyl oxygen, phenyl, or alkoxy; alkenyl optionally substituted by phenyl; hydroxy; alkoxy; alkanoyloxy; alkenyloxy; nitro; —$NR_1R_2$ or hydroxyalkoxy,
  $R_1$ and $R_2$, which may be the same or different, are each hydrogen or alkyl,
and pharmaceutically acceptable derivatives thereof.

There are also described processes for making the compounds and pharmaceutical, e.g. anti-allergic, compositions containing the compounds.

8 Claims, No Drawings

COMPOUNDS

This invention relates to new compounds, to methods of their preparation and to compositions containing them.

According to our invention we provide compounds of formula I,

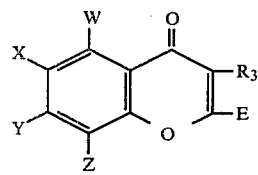   I in which E is a —COOH, a 5-tetrazolyl or an (N-tetrazol-5-yl) carboxamido group, R₃ is hydrogen or alkyl, an adjacent pair of W, X, Y and Z form a 5 membered chain comprising alkylene groups and optionally one or two oxygen atoms, the chain optionally being substituted by one or two alkyl groups, the remaining substituents W, X, Y or Z are hydrogen; halogen; alkyl optionally substituted by one or more of the groups hydroxy, halogen, carbonyl oxygen, phenyl, or alkoxy; alkenyl optionally substituted by phenyl; hydroxy; alkoxy; alkanoyloxy; alkenyloxy; nitro; —NR₁R₂; or hydroxyalkoxy, R₁ and R₂, which may be the same or different, are each hydrogen or alkyl, and pharmaceutically acceptable derivatives thereof.

According to our invention we also provide a process for the production of a compound of formula I, or a pharmaceutically acceptable derivative thereof, which comprises (a) producing a compound of formula I in which E is a —COOH group by cyclising a compound of formula II,

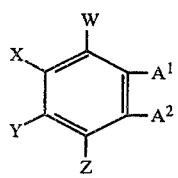   II in which W, X, Y and Z are as defined above,

A¹ and A² represent the pairs of groups, (i) —COCHR₃COCOR″ and —OM or a halogen atom, or (ii) —H and —O—C(COR″)=CR₃—COR″

R₃ is as defined above,

R″ represents —OM, or a group which is hydrolysable thereto, and

M represents hydrogen or an alkali metal, and if necessary or desired hydrolysing the group —COR″, to a group —COOM, (b) producing a compound of formula I in which E is a —COOH group by selectively hydrolysing a compound of formula III,

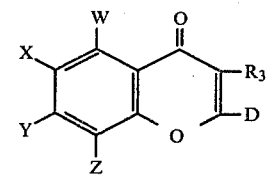   III in which R₃, W, X, Y and Z are as defined above, and

D is a group hydrolysable to a —COOH group, (c) producing a compound of formula I in which E is a 5-tetrazolyl group by reacting a compound of formula IV,

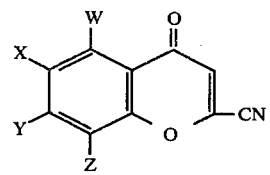   IV in which W, X, Y and Z are as defined above, with an azide in a solvent which is inert under the reaction conditions, or (d) producing a compound of formula I in which E is an (N-tetrazol-5-yl)carboxamido group by reacting a compound of formula V,

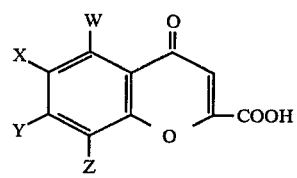   V or an acid halide, ester or mixed anhydride thereof, in which W, X, Y and Z are as defined above, with 5-aminotetrazole, and where desired or necessary converting the compound of formula I to a pharmaceutically acceptable derivative thereof.

When A₂ is a group —OM the cyclisation of process (a)(i) may be carried out by heating, or under basic or neutral conditions. It is however preferred to carry out the cyclisation in the presence of an acid, e.g. hydrochloric acid, and in a solvent which is inert under the reaction conditions, e.g. ethanol. The reaction may be carried out at from about 20° to 150° C. The group —COR″ is preferably an ester group, e.g. R″ may be a lower alkoxy group. When A₂ is halogen the cyclisation may be carried out in a solvent which is inert under the reaction conditions, preferably a high boiling polar solvent, e.g. pyridine, dimethylformamide or hexamethylphosphoramide. The reaction is preferably carried out with the aid of a strong base, for example an alkali metal, e.g. sodium, hydride. The reaction is preferably carried out at a temperature of from about 80° to 200° C., in the absence of free oxygen, e.g. under an inert atmosphere such as nitrogen.

The cyclisation of process (a)(ii) may be carried out by treating the compound of formula II with a cyclising agent, for example a dehydrating agent such as chlorosulphonic, polyphosphoric or sulphuric acid. The reaction is preferably carried out under anhydrous conditions and may be carried out at a temperature of from 0° to 100° C. Alternatively cyclisation may be achieved by converting the free carboxy groups of the compound of formula II to acyl halide groups and subjecting the resulting acyl halide to an intramolecular Friedel-Crafts reaction.

In process (b) the group D may be, for example, an ester, acid halide, amide or a nitrile group, which may be hydrolysed to a —COOH group. The hydrolysis may be carried out using conventional techniques, for example under mildly basic conditions, e.g. using sodium carbonate, sodium hydroxide, sodium bicarbonate, or under acidic conditions, e.g. a mixture of aqueous dioxan and hydrochloric acid, or hydrogen bromide in acetic acid. The hydrolysis may be carried out at a temperature of from about 25° to 120° C. depending on the compounds used.

Suitable solvents which are inert under the reaction conditions of process (c) include those in which both the reagents are soluble, e.g. N,N-dimethylformamide. Other solvents which may be mentioned include dimethylsulphoxide, tetrahydrofuran, diethyl glycol and ethyl methyl glycol. The reaction is preferably carried out at a temperature of from about 20° to 130° C. for from about 1 to 20 hours. The azide used in the reaction is preferably ammonium or an alkali metal azide, e.g. sodium or lithium azide, but other azides, e.g. aluminium azide or the azides of nitrogen containing bases, e.g. mono-, di-, tri-, and tetra- methyl- ammonium, anilinium, morpholinium and piperidinium azides, may also be used if desired. Where an azide other than that of an alkali metal is used this azide may be prepared in the reaction mixture by double decomposition. The reaction may, if desired, be carried out in the presence of an electron acceptor, e.g. aluminium chloride, boron trifluoride, ethyl sulphonic acid or benzene sulphonic acid. As an alternative to the reaction conditions set out above, the reaction may be carried out using hydrazoic acid (hydrogen azide) at a temperature of from about 20° to 150° C. in a suitable solvent, under greater than atmospheric pressure. When an azide other than hydrazoic acid is used, e.g. sodium azide, the product of the reaction will be the corresponding tetrazole salt. This salt may readily be converted to the free acid by treatment with strong acid, e.g. hydrochloric acid.

In process (d) the anhydride is preferably a mixed anhydride of such a type that it will cleave preferentially, to give the desired chromone carboxamidotetrazole, as the major product when reacted with the 5-aminotetrazole. Examples of suitable acids from which the mixed anhydride may be derived are sulphonic acids e.g. benzene sulphonic acid, sterically hindered carboxylic acids, e.g. pivalic, isovaleric, diethylacetic or triphenylacetic acid, and alkoxy formic acids, e.g. a lower alkoxy formic acid such as ethoxy or isobutoxy formic acid. When an acid halide is used it may conveniently be an acid chloride. The reaction is preferably carried out under anhydrous conditions in a solvent which will not react with either the 5-aminotetrazole or the mixed anhydride or acid halide, e.g. pyridine or dimethylformamide. However when the reaction is carried out in a non-basic solvent, e.g. dimethylformamide, an adequate proportion of an acid acceptor, e.g. triethylamine, should also preferably be present. The reaction is preferably carried out at a temperature of from about −15° to +20° C. When an ester is used we prefer to use a lower alkoxy ester and to carry out the reaction in a solvent which is inert under the reaction conditions, e.g. glacial acetic acid, at a temperature of from about 100° to 150° C. When a compound of formula V itself is used the reaction may be carried out by heating the compound of formula V and the 5-aminotetrazole in a solvent which is inert under the reaction conditions, e.g. dimethylacetamide, at a temperature of from 100° to 200° C. Alternatively the reaction may be carried out in the presence of a condensation agent, e.g. N,N'-carbonyl-diimidazole or dicyclohexyl carbodiimide, in an aprotic solvent, e.g. dimethylformamide, at a temperature of from about 10° to 40° C.

The compounds of formula II, in which $A^1$ and $A^2$ represent the groups —COCHR$_3$COCOR'' and —OM or halogen, may be made by reacting a compound of formula VI,

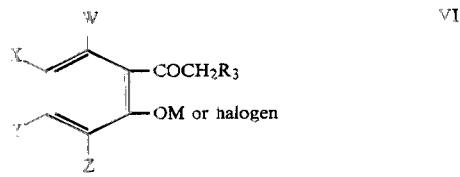

in which $R_3$, W, X, Y, Z, and M are as defined above, with a compound of formula VII,

in which R'' is as defined above,
R' is a suitable leaving group, e.g. an alkoxy, halo, amino, alkylamino, substituted amino (e.g. an arylsulphonylamino group) or substituted alkylamino group, reactive with the carbanion of the —COCH$_2$R$_3$ group of the compound of formula VI, and
each Z is a carbonyl oxygen atom, or one Z may represent two halogen atoms and the other a carbonyl oxygen atom,
and if necessary hydrolysing the resulting compound to a compound of formula II. The preferred compounds of formula VII are dialkyl oxalates, e.g. diethyl oxalate.

The compounds of formula III may be made in a manner analogous to process (a)(i) using a starting material of formula VIII,

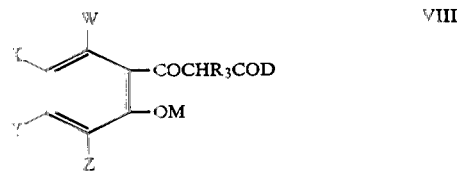

in which $R_3$, W, X, Y, Z, M and D are as defined above.

The compounds of formula VIII may be made from known compounds in a manner analogous to that described above for the preparation of the corresponding compounds of formula II, using a compound of formula R'COD in which R' and D are as defined above, in place of the compound of formula VII.

Alternatively the compounds of formula III may, for example in the case of the acid halide, the amide and the nitrile, be made from compounds of formula I using conventional techniques, e.g. reaction of an ester of the compound of formula I with ammonia to produce the amide, followed by dehydration of the amide to form the nitrile.

The compounds of formula II in which $A^1$ and $A^2$ represent —H and —O—C(COR″)=CR$_3$—COR″ may be made from known compounds using methods known per se, e.g. by reaction of an appropriately substituted phenol with a dialkyl ester of acetylene di-carboxylic acid followed, if necessary, by hydrolysis.

The compounds of formula IV may be made by dehydrating the corresponding chromone amide using, for example, phosphorus oxychloride, as dehydrating agent. The reaction is preferably carried out using at least one molar equivalent of dehydrating agent per mole of the chromone amide. Where the dehydrating agent reacts with one of W, X, Y or Z (e.g. a substituent comprising an —OH group) sufficient dehydrating agent should be used to satisfy the side reaction as well as the main reaction. The reaction may, if desired, be carried out in the presence of an acid binding agent, e.g. triethylamine. The reaction may be carried out in the presence of a solvent, e.g. N,N-dimethylformamide, dimethyl sulphoxide, pyridine, benzene or hexamethyl phosphoramide, or an excess of the dehydrating agent may be used as the reaction medium. The reaction may be carried out at a temperature of from about 0° to 200° C. depending on the dehydrating agent used. When phosphorus oxychloride is used a temperature of from 0° to 100° C. is preferred.

The chromone amide starting materials may be made by reacting a corresponding chromone ester with ammonia, using techniques conventional in the production of amides from esters, e.g. using an alkanol as solvent at a temperature of 0° to 120° C.

The chromone ester starting materials may be made by process (a)(i) above.

The compounds of formula I and the intermediates therefor may be isolated from their reaction mixtures using conventional techniques.

Pharmaceutically acceptable derivatives of the compounds of formula I include pharmaceutically acceptable salts, and, when E is a —COOH group, esters and amides of the 2-carboxylic acid group. Suitable salts include ammonium, alkali metal (e.g. sodium, potassium and lithium) and alkaline earth metal salts (e.g. calcium or magnesium), and salts with suitable organic bases, e.g. salts with hydroxylamine, lower alkylamines such as methylamine or ethylamine, with substituted lower alkylamines, e.g. hydroxy substituted alkylamines such as tris(hydroxymethyl)methylamine, or with simple monocyclic nitrogen heterocyclic compounds, e.g. piperidine or morpholine. Suitable esters include simple lower alkyl esters, e.g. the ethyl ester, esters derived from alcohols containing basic groups, e.g. di-lower alkyl amino substituted alkanols such as the β-(diethylamino)-ethyl ester, and acyloxy alkyl esters, e.g. a lower acyloxy-lower alkyl ester such as the pivaloyloxymethyl ester, or a bis-ester derived from a di-hydroxy compound, e.g. a di(hydroxy-lower alkyl) ether, e.g. the bis-2-oxapropan-1,3-diyl ester. The pharmaceutically acceptable acid addition salts of the basic esters, and also of those compounds in which $R_5$ is a group —NR$_1$R$_2$, e.g. the hydrochloride, the hydrobromide, the oxalate, the maleate or the fumarate may also be used. The esters may be made by conventional techniques, e.g. esterification, transesterification or reaction of the acid, or a salt thereof, with an appropriate compound containing a good leaving group. The amides may be, for example, unsubstituted or mono- or di- C 1 to 6 alkyl amides and may be made by conventional techniques, e.g. reaction of an ester of the corresponding acid with ammonia or an appropriate amine.

The compounds of formula I and pharmaceutically acceptable derivatives thereof are useful because they possess pharmacological activity in animals; in particular they are useful because they inhibit the release and/or action of pharmacological mediators which result from the in vivo combination of certain types of antibody and specific antigen e.g. the combination of reaginic antibody with specific antigen (see Example 27 of British Patent Specification No. 1,292,601). The compounds also possess theophylline type activity in that they inhibit the biological action of the enzyme cyclic adenosine monophosphate phosphodiesterase (See Example A). In man, both subjective and objective changes which result from the inhalation of specific antigen by sensitised subjects are inhibited by prior administration of the new compounds. Thus the new compounds are indicated for use in the treatment of asthma, e.g. allergic asthma. The new compounds are also indicated for use in the treatment of so-called 'intrinsic' asthma (in which no sensitivity to extrinsic antigen can be demonstrated). The new compounds are also of value in the treatment of other conditions in which antigen-antibody reactions are responsible for disease, for example, hay fever; certain eye conditions, e.g. trachoma; allimentary allergy, e.g. urticaria and atopic eczema; and gastrointestinal allergy, especially in children, e.g. milk allergy and ulcerative colitis.

For the above mentioned uses the dosage administered will, of course, vary with the compound employed, the mode of administration and the treatment desired. However, in general, satisfactory results are obtained when the compounds are administered at a dosage of from 0.1 to 50 mg per kg of animal body weight in the test set out in Example 27 of British Patent Specification No. 1,292,601. For man the indicated total daily dosage is in the range of from 1 mg to 3,500 mg preferably from 1 mg to 3,000 mg and more preferably from 1 mg to 600 mg, which may be administered in divided doses from 1 to 6 times a day or in sustained release form. Thus unit dosage forms suitable for administration (by inhalation or oesophageally) comprise from 0.17 mg to 600 mg, preferably 0.17 mg to 500 mg and more preferably from 0.17 mg to 100 mg of the compound preferably admixed with a solid or liquid pharmaceutically acceptable diluent, carrier or adjuvant.

The compounds of formula I, and pharmaceutically acceptable derivatives thereof have the advantage that they are more efficacious in certain pharmalogical models or are more readily absorbed, or are longer acting as measured by plasma half-life or are more active than compounds of similar structure.

We prefer each of $R_3$, and those of W, X, Y and Z which do not form part of a chain, and $R_1$ and $R_2$ to contain up to 10, and more preferably up to 6 carbon atoms.

Preferred compounds of formula I are those in which,

W is hydrogen, hydroxy, alkoxy, alkanoyloxy, alkenyloxy, nitro, —NR$_1$R$_2$, halogen, alkyl, hydroxyalkyl or hydroxyalkoxy, an adjacent pair of X, Y and Z form a 5 membered chain comprising alkylene groups and optionally one or two oxygen atoms, the chain optionally being substituted by one or two alkyl groups, and the remaining substituent X or Z is hydrogen; halogen; alkyl optionally substituted by one or more of the groups hydroxy, halogen, carbonyl oxygen, phenyl, or alkoxy; or alkenyl optionally substituted by phenyl.

Preferred values of the substituents in formula I are:

W=hydrogen; hydroxy; alkoxy C 1 to 3, e.g. methoxy or propoxy; allyloxy; nitro; amino; mono- or di-alkyl C 1 to 4 amino, e.g. dimethylamino or monoethylamino; chlorine or fluorine; straight or branched alkyl C 1 to 4, e.g. methyl; hydroxy-alkyl C 1 to 4, e.g. hydroxy-methyl; or hydroxy-alkoxy C 1 to 4, e.g. 2-hydroxy-propoxy, an adjacent pair of X, Y and Z (and more preferably X and Y) form a chain $-(CH_2)_5-$ or $-O-(CH_2)_4-$ or such a chain substituted by one or two methyl or ethyl groups, and the remaining substituent X or Z represents hydrogen; straight or branched alkyl C 1 to 8, e.g. ethyl, n-propyl or n-hexyl; allyl or hex-1-enyl; halogen, e.g. bromine or chlorine; mono- or di-hydroxyalkyl C 1 to 4, e.g. 2-hydroxy-propyl; chloro-alkyl C 1 to 4, e.g. chloro-propyl; chlorohydroxyalkyl C 1 to 4, e.g. chloro-hydroxypropyl; phenylalkyl in which the alkyl contains from 1 to 3 carbon atoms, e.g. benzyl or phenylethyl; styryl; or alkoxy C 1 to 4-alkyl C 1 to 4, e.g. ethoxy-methyl.

Particularly preferred compounds are those in which W is hydrogen, hydroxy, amino, mono- or di-alkyl amino, fluorine or alkoxy and the substituent X or Z which does not form part of a chain is propyl and an adjacent pair of X, Y and Z form a $-(CH_2)_5-$chain.

Especially preferred compounds of formula I are those in which W is hydrogen or hydroxy.

Specifically we prefer W to be hydrogen, X and Y together to form a $-(CH_2)_5-$chain, and Z to be alkyl C 1 to 6, preferably C 2 to 4, e.g. propyl.

We prefer E to be a $-COOH$ group and we also prefer the free acids of formula I.

According to our invention we also provide a process for the production of a pharmaceutically acceptable salt of a compound of formula I, which comprises reacting a compound of formula I, or another salt thereof, with a compound containing a pharmaceutically acceptable cation and capable of converting the compound of formula I, or the other salt thereof, to the desired pharmaceutically acceptable salt. In general we prefer to form the pharmaceutically acceptable salt by treating the free acid of formula I with an appropriate base, e.g. with an alkaline-earth or alkali metal hydroxide, carbonate or bicarbonate in aqueous solution or by a metathetical process with an appropriate salt. When a strongly basic compound is used care should be taken, e.g. by keeping the temperature sufficiently low, to ensure that the compound of formula I is not hydrolysed or otherwise degraded. The pharmaceutically acceptable salt may be recovered from the reaction mixture by, for example, solvent precipitation and/or removal of the solvent by evaporation, e.g. by freeze drying.

According to our invention we also provide a pharmaceutical composition comprising (preferably less than 80%, and more preferably less than 50% by weight) of a compound of formula I, or a pharmaceutically acceptable derivative thereof, in combination with a pharmaceutically acceptable adjuvant, diluent or carrier. Examples of suitable adjuvants, diluents or carriers are: for tablets and dragees; microcrystalline cellulose, calcium phosphate, diatomaceous earth, mannitol, talc or stearic acid; for capsules, tartaric acid or lactose; for suppositories; natural or hardened oils or waxes; and for inhalation compositions, coarse lactose. The compound of formula I, or the pharmaceutically acceptable derivative thereof, preferably has a mass median diameter of from 0.01 to 10 microns. The compositions may also contain suitable preserving, stabilising and wetting agents, solubilizers, sweetening and colouring agents and flavourings. The compositions may, if desired, be formulated in sustained release form. We prefer compositions which are designed to be taken oesophageally and to release their contents in the gastrointestinal tract.

According to the invention we also provide bio-precursors, i.e. compounds which are broken down in the animal body to compounds of formula I. We also provide metabolites of the compounds of formula I, i.e. those compounds to which the compounds of formula I are converted by the animal body before excretion.

Some of the compounds of formula I are asymmetric and may therefore exist in the form of two (or more) optical isomers or a racemic or other mixture of such isomers. The various optical isomers may be resolved, wholly or partially, using conventional techniques, e.g. formation of a salt with an optically active base, e.g. cinchonidine, fractional crystallisation of the salt and subsequent regeneration of the free acid.

The 5-tetrazolyl and (N-tetrazol-5-yl)carboxamide groups are of formulae IX and X respectively,

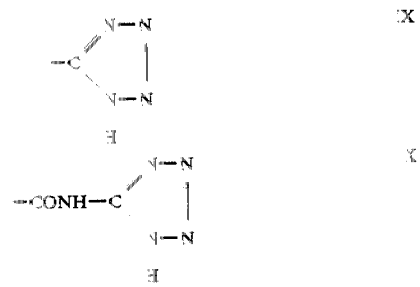

the groups of formulae IX and X may exist in other tautomeric forms and such other tautomeric forms are included within the definition of the compounds of formula I.

EXAMPLE 1

7,8,9,10-Tetrahydro-4-oxo-4H, 6H-cyclohepta[g]-1-benzopyran-2-carboxylic acid (a) 6,7,8,9-Tetrahydro-1-methoxy-5-oxo-5H-benzocycloheptadiene (30 gm) in dioxan (100 ml) was added to zinc amalgam prepared from zinc (29.7 gm) and mercuric chloride (3 gm). The reaction mixture was heated under reflux for eight hours and cooled to room temperature. The supernatant liquid was decanted off and the residual amalgam was washed with a small volume of aqueous dioxan. The liquors were combined and extracted with ethyl acetate. The extracts were washed with brine and water and dried over magnesium sulphate. Removal of the solvent in vacuo yielded a pale green mobile oil. Wt=24.1 gm.

The structure of the product was confirmed by IR and NMR.

(b)

2-Acetyl-3-hydroxy-6,7,8,9-tetrahydro[5H]-benzocycloheptadiene

The product from step (a) (36 gm) was dissolved in dichloromethane (200 ml) and cooled to $-20°$ C. Titanium tetrachloride (114 gm) was added dropwise and the reaction mixture was stirred for 15 minutes. Acetyl chloride (39.25 gm) was then added and the reaction mixture was stirred at −20° C. for a further 90 minutes. Boron trichloride (25 gm) was added and the reaction was stirred at −20° C. for fifteen minutes and then allowed to reach room temperature. The reaction mixture was poured onto ice and extracted with dichloromethane. The organic extracts were washed with brine and water and then dried over magnesium sulphate. Removal of the solvent in vacuo yielded an oil which solidified on standing and was crystallized from 60°/80° C. petroleum ether to give the title compound. Wt=30.6 gm. Mpt=94°–95° C.

$C_{13}H_{16}O_2$ Calc: C 76.5%; H 7.8%; Found: C 76.6%; H 8.1%.

(c) Ethyl 7,8,9,10-tetrahydro-4-oxo-4H,6H-cyclohepta[g]-1-benzopyran-2-carboxylate A solution of the product from step (b) (10 gm) in ethanol (50 ml) was added to sodium ethoxide solution (prepared by dissolving sodium (5.75 gm) in ethanol (150 ml)) and stirred at room temperature for ten minutes. Diethyl oxalate (17.5 gm) in ethanol (30 ml) was added dropwise and the reaction mixture was refluxed for 90 minutes, cooled, poured into dilute hydrochloric acid and extracted with chloroform. Removal of the chloroform in vacuo yielded a brown oil which was refluxed with ethanol (150 ml) containing conc. hydrochloric acid (80 ml) for five hours. The bulk of the solvent was removed in vacuo and the residues were poured into water and extracted with ethyl acetate. After washing with brine and water the ethyl acetate was removed in vacuo yielding a brown oil which was found to contain the chromone ester and the chromone acid. Trituration of the oil with 40°/60° C. petroleum ether yielded the title compound, a fawn coloured solid which was crystallised from aqueous ethanol. Wt 0.34 gm. Mpt. 74°–75° C.

$C_{17}H_{18}O_4$ Calc: C 71.3%; H 6.3%; Found: C 71.3%; H 6.5%.

The corresponding chromone acid was obtained by crystallisation of the residues which yielded the chromone ester. Wt=1.2 gm. Mpt=242° C. (d).

$C_{15}H_{14}O_4$ Calc: C 69.8%; H 5.4%; Found: C 69.5%; H 5.5%.

The acid was converted to the sodium salt by treatment with aqueous sodium bicarbonate solution. Wt=1.1 gm.

$C_{15}H_{13}NaO_4$ Calc: C 64.3%; H 4.7%; Found: C 60.7%; H 5.0%.
for 5.6%$H_2O$ C 60.7%; H 5.1%.

EXAMPLE 2

7,8,9,10-Tetrahydro-4-oxo-11-propyl-4H,6H-cyclohepta[g]-1-benzopyran-2-carboxylic acid (a) 2-Acetyl-3-allyloxy-6,7,8,9-tetrahydro-[5H]-benzocycloheptene The product from Example 1(b) 14 gm and anhydrous potassium carbonate (18.4 gm) were stirred together in dimethylformamide (300 ml) containing allyl bromide (20 ml) at room temperature for 48 hours. The reaction mixture was poured into a large volume of water and extracted with ether. The ethereal extracts were washed with 5% NaOH, brine and water and dried over MgSO$_4$. Removal of the ether in vacuo yielded an oil which solidified on standing and was crystallised from 60°/80° C. petroleum ether to yield the title compound as yellow needles. Wt=9.9 gm. Mpt 58°–60° C.

$C_{16}H_{20}O_2$ Calc: C 78.7%; H 8.2%; Found: C 78.7%; H 8.3%.

(b) 2-Acetyl-1-allyl-3-hydroxy-6,7,8,9-tetrahydro-[5H]-benzocycloheptene

The product from step (a) (15 gm) was heated at 200° C. under an atmosphere of hydrogen for two hours. The product was purified by column chromatography which gave a straw coloured mobile oil.
Wt=14.1 gm.

The structure of the product was confirmed by NMR.

(c) 2-Acetyl-3-hydroxy-1-propyl-6,7,8,9-tetrahydro-[5H]-benzocycloheptene

The product from step (b) (12 gm) was dissolved in ethanol (150 ml) and reduced with 5% palladium on carbon (1.2 gm) under an atmosphere of hydrogen (45 psi). The catalyst was removed by filtration and the ethanol was removed in vacuo to yield the product as a brown mobile oil. Wt 11.5 gm.

The structure of the product was confirmed by NMR.

(d) 7,8,9,10-Tetrahydro-4-oxo-11-propyl-4H,6H-cyclohepta[g]-1-benzopyran-2-carboxylate The product from step (c) (10 gm) in ethanol (25 ml) was added dropwise to a stirred solution of sodium (4.6 gm) in ethanol (100 ml) and stirred at room temperature for five minutes. Diethyloxalate (14.8 gm) in ethanol (15 ml) was added and the reaction mixture was heated at 100° C. for three hours. The reaction mixture was cooled and water was added followed by dilute hydrochloric acid. The reaction mixture was then extracted with chloroform. Removal of the chloroform in vacuo yielded a pale brown oil which was heated under reflux with ethanol (50 ml) containing conc. hydrochloric acid (1 ml) for 60 minutes. The ethanol was removed in vacuo, water was added and the mixture was then extracted with ethyl acetate. Removal of the ethyl acetate yielded a brown solid which was heated at 100° C. with sodium bicarbonate (1 gm) in aqueous ethanol for 60 minutes. The ethanol was removed in vacuo and the residue was acidified with dilute hydrochloric acid. The precipitated product was collected, washed with water, dried in vacuo and crystallised from ethanol to yield the title compound. Wt=1.8 gm.

The structure of the product was confirmed by NMR and MS.

The sodium salt was prepared by treating the acid (1.2 gm) with an equivalent amount of aqueous sodium bicarbonate. Wt=1.1 gm.

$C_{18}H_{19}NaO_4$: Required: C 67.0%; H 5.9%; Found: C 65.4%; H 5.7%; 2.4% H$_2$O: C 65.4%; H 6.0%.

EXAMPLE 3

The following compounds made by the above processes:
(a) 5-Hydroxy-7,8,9,10-tetrahydro-4-oxo-11-propyl-4H,6H-cyclohepta-[g]-1-benzopyran-2-carboxylic acid.

(b) 7,8,9,10-Tetrahydro-4-oxo-11-propyl-4H,6H-cyclohepta[g]-1-benzopyran-2-[N-(tetrazol-5-yl)]carboxamide.

(c) 5-(5-Hydroxy-7,8,9,10-tetrahydro-4-oxo-11-propyl-4H,6H-cyclohepta[g]-1-benzopyran-2-yl)tetrazole.

EXAMPLE A

Effect of compounds upon cyclic adenosine monophosphate phosphodiesterase

The enzyme used is beef heart cyclic 3',5'-nucleotide phosphodiesterase (supplied by Sigma). TRIS is 2-amino-2-(hydroxymethyl)-propane-1,3-diol.

Assay principle: adenosine 3',5'-cyclic monophosphate is converted into 5'-adenosine monophosphate by phosphodiesterase. The formed adenosine monophosphate is further converted into adenosine+phosphate by snake venom 5'-nucleotidase. The amount of phosphate formed is quantitated and this is a reflection of phosphodiesterase activity.

Phosphodiesterase assay is carried out in the following way at 37° C.-all reagents are in 40 mM TRIS-HCl pH 7.4 buffer. The reaction mixture contains phosphodiesterase (0.25 mg at 0.38 units/mg)-0.25 ml, $MgSO_4$ (2 mM)—0.1 ml, Venom (2 mg/ml Ophiophagus hannan Sigma)—0.05 ml, inhibitor or TRIS—0.5 ml. Adenosine 3',5'-cyclic monophosphate (5 mM)—0.1 ml, is added to start the reaction. The reaction is terminated after 30 minutes with trichloroacetic acid (55%)—0.1 ml. The precipitated protein is removed by centrifugation and the supernatant removed. The amount of phosphate released is assayed by mixing 0.5 ml of the trichloroacetic acid supernatant with 0.5 ml 1 N $H_2SO_4$, 0.1 ml 5% ammonium molybdate and 0.1 ml 5% ascorbic acid, and the absorbance of the solution at 650 nm is measured after 15 minutes.

The concentration of the compound required to produce a 50% inhibition ($IC_{50}$) of phosphodiesterase activity is measured by this procedure.

Compounds such as Theophylline, which are used in the treatment of asthma inhibit the biological activity of the enzyme cyclic adenosine monophosphate phosphodiesterase. The connection between the inhibition of adenosine monophosphate phosphodiesterase activity and anti-asthmatic activity is also illustrated by James E Tateson et al Life Sciences Vol. 18 pp 153-162 and J C Foreman et al British Medical Journal, 1976, 1, pages 820-821.

We claim:

1. A compound having the formula

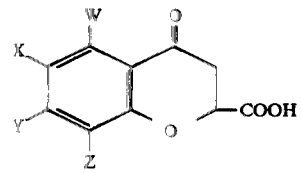

in which

W is hydrogen or hydroxy, an adjacent pair of X, Y and Z form a pentamethylene chain, the remaining substituent X or Z is hydrogen or alkyl $C_1$ to $C_{10}$, and pharmaceutically acceptable derivatives thereof.

2. A compound according to claim 1, wherein the remaining substituent X or Z which does not form part of a chain is alkyl $C_1-C_6$.

3. A compound according to claim 1, wherein X and Y together form a $(CH_2)_5$—chain.

4. A compound according to claim 2, wherein the substituent X or Z which does not form part of a chain is propyl.

5. A compound according to claim 1, wherein X and Y together form a—$(CH_2)_5$—chain and Z is alkyl C 1 to 6.

6. A compound according to claim 1 which is 7,8,9,10-tetrahydro-4-oxo-4H, 6H-cyclohepta-1-benzopyran-2-carboxylic acid, 7,8,9,10-tetrahydro-4-oxo-11-propyl-4H,6H-cyclohepta-benzopyran-2-carboxylic acid, or 5-hydroxy-7,8,9,10-tetrahydro-4-oxo-11-propyl-4H,6H-cyclohepta-1-benzopyran-2-carboxylic acid.

7. An anti-allergic pharmaceutical composition comprising up to 80% by weight of a compound according to claim 1, as active ingredient, in combination with a pharmaceutically acceptable adjuvant, diluent or carrier.

8. A method of treating asthma, hay fever, trachoma, alimentary allergy or gastrointestinal allergy which comprises administering an effective amount of a compound according to claim 1 to a mammal suffering from such a condition.

* * * * *

UNITED STATES PATENT AND TRADEMARK OFFICE
CERTIFICATE OF CORRECTION

PATENT NO. : 4,211,788
DATED : July 8, 1980
INVENTOR(S) : HUGH CAIRNS ET AL.

It is certified that error appears in the above—identified patent and that said Letters Patent are hereby corrected as shown below:

Col. 12, lines 8-9 (formula),

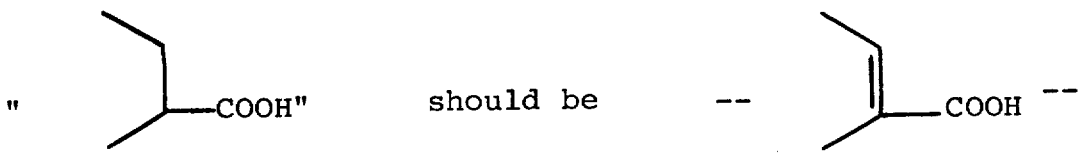

Col. 12, line 33, "cyclohepta-1", should be --cyclohepta[g]-1-- (Claim 6).

Col. 12, line 36, "benzopyran", should be --[g]-benzopyran-- (Claim 6).

Col. 12, line 38, "cyclohepta-1", should be --cyclohepta[g]-1-- (Claim 6).

Signed and Sealed this

Third Day of February 1981

[SEAL]

Attest:

RENE D. TEGTMEYER

Attesting Officer    Acting Commissioner of Patents and Trademarks